US010955907B2

(12) United States Patent
Chong et al.

(10) Patent No.: US 10,955,907 B2
(45) Date of Patent: Mar. 23, 2021

(54) VR MOVEMENT PLATFORM

(71) Applicant: International Business Machines Corporation, Armonk, NY (US)

(72) Inventors: Liu Chong, Xian (CN); Jin Xa Xu, Xian (CN); Jia Zhong Wu, Xian (CN); Juan Wu, Xian (CN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/184,486

(22) Filed: Nov. 8, 2018

(65) Prior Publication Data

US 2020/0150748 A1    May 14, 2020

(51) Int. Cl.
*G06F 3/01* (2006.01)
*G06F 3/033* (2013.01)

(52) U.S. Cl.
CPC ............ *G06F 3/011* (2013.01); *G06F 3/0334* (2013.01)

(58) Field of Classification Search
None
See application file for complete search history.

(56) References Cited

U.S. PATENT DOCUMENTS

| | | |
|---|---|---|
| 4,951,034 A | 8/1990 | Mazzone et al. |
| 5,541,621 A | 7/1996 | Nmngani |
| 6,135,928 A | 10/2000 | Butterfield |
| 6,408,156 B1 | 6/2002 | Miyazaki et al. |
| 7,387,592 B2 | 6/2008 | Couvillion, Jr. et al. |
| 9,766,460 B2 | 9/2017 | Burns et al. |
| 10,081,495 B2 | 9/2018 | Moller |
| 2003/0232698 A1 | 12/2003 | Couvillion, Jr. et al. |
| 2007/0109259 A1* | 5/2007 | Liu .......................... G06F 3/011 345/156 |
| 2007/0114861 A1 | 5/2007 | Bolt et al. |
| 2008/0084387 A1 | 4/2008 | Mcardle |
| 2009/0058855 A1 | 3/2009 | Mishra et al. |
| 2009/0171173 A1 | 7/2009 | Baker, Jr. et al. |
| 2011/0009241 A1* | 1/2011 | Lane .................. A63B 24/0087 482/8 |
| 2013/0257719 A1 | 10/2013 | Jangaard et al. |

(Continued)

FOREIGN PATENT DOCUMENTS

WO    2016153442 A1    9/2016

OTHER PUBLICATIONS

Unknown, "Be Fearless in VR—Run, Crouch and Jump Virtuix Omni Trailer," YouTube, Jul. 20, 2018, 3 pages. https://www.youtube.com/watch?v=R_u3Ciz_iQs.

(Continued)

*Primary Examiner* — Amare Mengistu
*Assistant Examiner* — Sarvesh J Nadkarni
(74) *Attorney, Agent, or Firm* — Jared C. Chaney

(57) ABSTRACT

In some embodiments, a movement platform may be used to develop force models for the determination of movement based on force patterns received from the movement platform. A force model is made by comparing a known user movement to force readings recorded during the user movement. Movement platform force readings may be compared to a plurality of force models to determine a user movement. Once a matching force model is determined, the matching force model may be used to generate instructions for moving a user on the movement platform.

20 Claims, 11 Drawing Sheets

(56) References Cited

U.S. PATENT DOCUMENTS

2017/0252642 A1 9/2017 Matina
2019/0134457 A1* 5/2019 Chen .................. G06F 3/011

OTHER PUBLICATIONS

Unknown, "Infinadeck | The only true VR omnidirectional treadmill," Infinadeck, Jul. 20, 2018, 3 pages http://www.infinadeck.com/.

Horwitz, "Kat Walk Mini promises a compact, affordable VR treadmill for in-game movement," Venture Beat, Apr. 5, 2018, 3 pages. https://venturebeat.com/2018/04/05/kat-walk-mini-promises-a-compact-affordable-vr-treadmill-for-in-game-movement/.

Unknown, "nature—events—friends," Logo Stir-der VR, Printed Aug. 3, 2018, 7 pages. https://www.stridervr.com/enjoy.

Mell et al., "The NIST Definition of Cloud Computing," Recommendations of the National Institute of Standards and Technology, U.S. Department of Commerce, Special Publication 800-145, Sep. 2011, 7 pgs.

Chong et al., "VR Movement Platform," U.S. Appl. No. 16/184,476, filed Nov. 8, 2018.

List of IBM Patents or Patent Applications Treated as Related, dated Nov. 8, 2018, 2 pages.

* cited by examiner

VR MOVEMENT PLATFORM

BACKGROUND

Aspects of the present disclosure relate to virtual reality systems, more particular aspects relate to user interaction devices.

A virtual reality system may utilize user interaction devices to record user actions and provide feedback to users. The user interaction devices are designed to provide an immersive experience for users in a virtual reality setting.

SUMMARY

The present invention provides the method using and computer program product of a virtual reality movement platform. Some embodiments of the present disclosure can be illustrated by a method comprising, monitoring, by a processor and during a first time period, a grid of a plurality of movement units on a movement platform, detecting, by a first force sensor on a first movement unit of the plurality of movement units, force data, wherein the force data comprises a first force exerted upon the first movement unit by a first user; receiving, by the processor, a first set of movement information of the first user for the first time period; and compiling, by the processor, the force data and the movement information into a first force model.

The present invention provides the method of using a virtual reality movement platform. Some embodiments of the present disclosure can be illustrated by a method comprising receiving, by a processor from a movement platform, force data of a user, comparing, by the processor, the force data to one or more force models in a model database, determining that the force data matches a first force model from the one or more force models, predicting, based on the comparing and the determining, a displacement for the user, calculating, based on the predicting, movement instructions for the movement platform, and sending, by the processor, movement instructions to the movement platform.

DETAILED DESCRIPTION

Figure 1A:
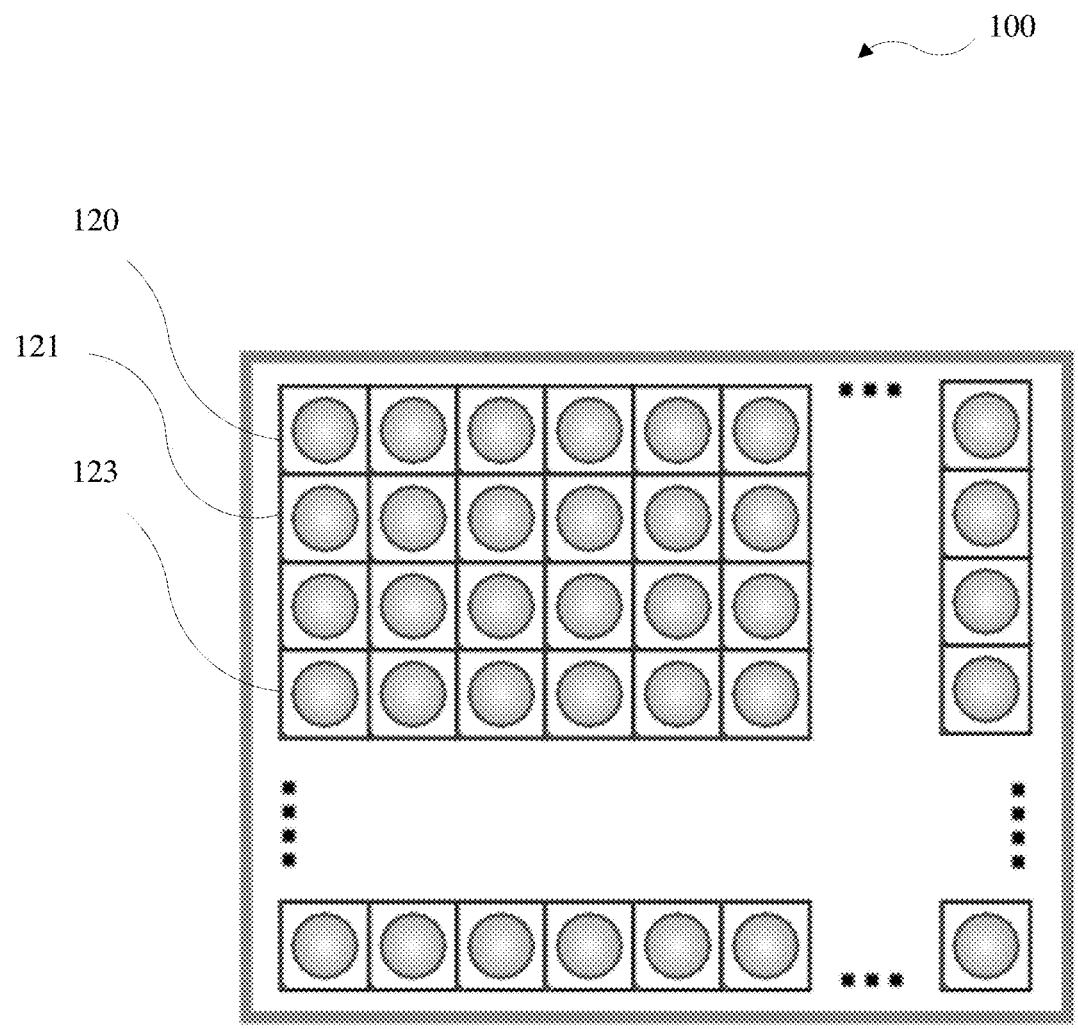
FIG. 1A illustrates an exemplary depiction of a movement platform with a plurality of movement units.

Aspects of the present disclosure relate to virtual reality systems, more particular aspects relate to movement platforms for user interactions. While the present disclosure is not necessarily limited to such applications, various aspects of the disclosure may be appreciated through a discussion of various examples using this context.

Virtual reality (VR) systems are designed with the intent to create an interactive and immersive environment for users. There are many approaches to capturing user activity and providing feedback to the user in a VR system, but current systems have limitations. For example, in a VR football training program, it may be beneficial for a user to be able to walk, run or jump freely. However, if the VR system is being used in a small room without a movement device or movement platform, it is likely that the user would hit a wall before scoring a touchdown. Current movement platforms, such as treadmills, provide for some degree of movement but do not have the feedback and sensor capabilities to provide a comprehensive force assessment of a user's actions, and may not fully facilitate freedom of movement actions such as twisting, running, and jumping.

Some embodiments of the present disclosure provide VR systems with a movement platform capable of receiving user force data and moving a user. The movement platform can read forces exerted by the user and activate motor components of the movement platform to simulate freedom of movement for a user by continuously repositioning the user over the center of the movement platform. In some embodiments, the movement platform includes of a grid of movement units. In some such embodiments, each movement unit can include of a sphere, two motors to rotate the sphere, and three sensors to detect movement or forces of the sphere. In some embodiments, the spheres are used to sense user movement.

For the purpose of this disclosure, horizontal forces (i.e., forces that are sufficiently parallel to the top surface of the movement platform) are described as X-forces and Y-forces. For example, "sufficiently parallel" could be described as within 10° of parallel. In some embodiments, X-forces are sufficiently perpendicular to Y-forces. For example, two surfaces that are sufficiently perpendicular could be described as offset 80-100° from each other. Forces sufficiently perpendicular to the top surface of the movement platform will be described as Z-Forces. In some embodiments, sensors are used to detect X-Forces, Y-Forces, and Z-Forces of a user's movements on the platform. In these embodiments, for example, a walking user would apply X-forces, Y-forces, and Z-forces with first a left foot and then a right foot. In some embodiments, the spheres are rotated to account for user movement. In these embodiments, for example, as a user takes a step, the movement system could roll the spheres that are in contact with the feet such that the user stays approximately positioned above the center of the movement platform. In some embodiments, the user platform is used to determine an expected force pattern for a variety of user movements. In some embodiments, a database of force models including force patterns and associated user movements is compiled by recording user movements on the movement platform and measuring the forces that are applied to the user platform in the same time period. In some embodiments, when forces are recorded on the user platform, they are compared to a database of force models and the force model that matches the recorded forces is used to estimate user movement. In some embodiments, the determined user movement is used to rotate the spheres in a manner that will keep the user's center of mass centered above the movement platform. In some embodiments, the determined user movement is sent to a computer system for 3-D imaging of a user in a virtual reality environment.

Figure 1B:
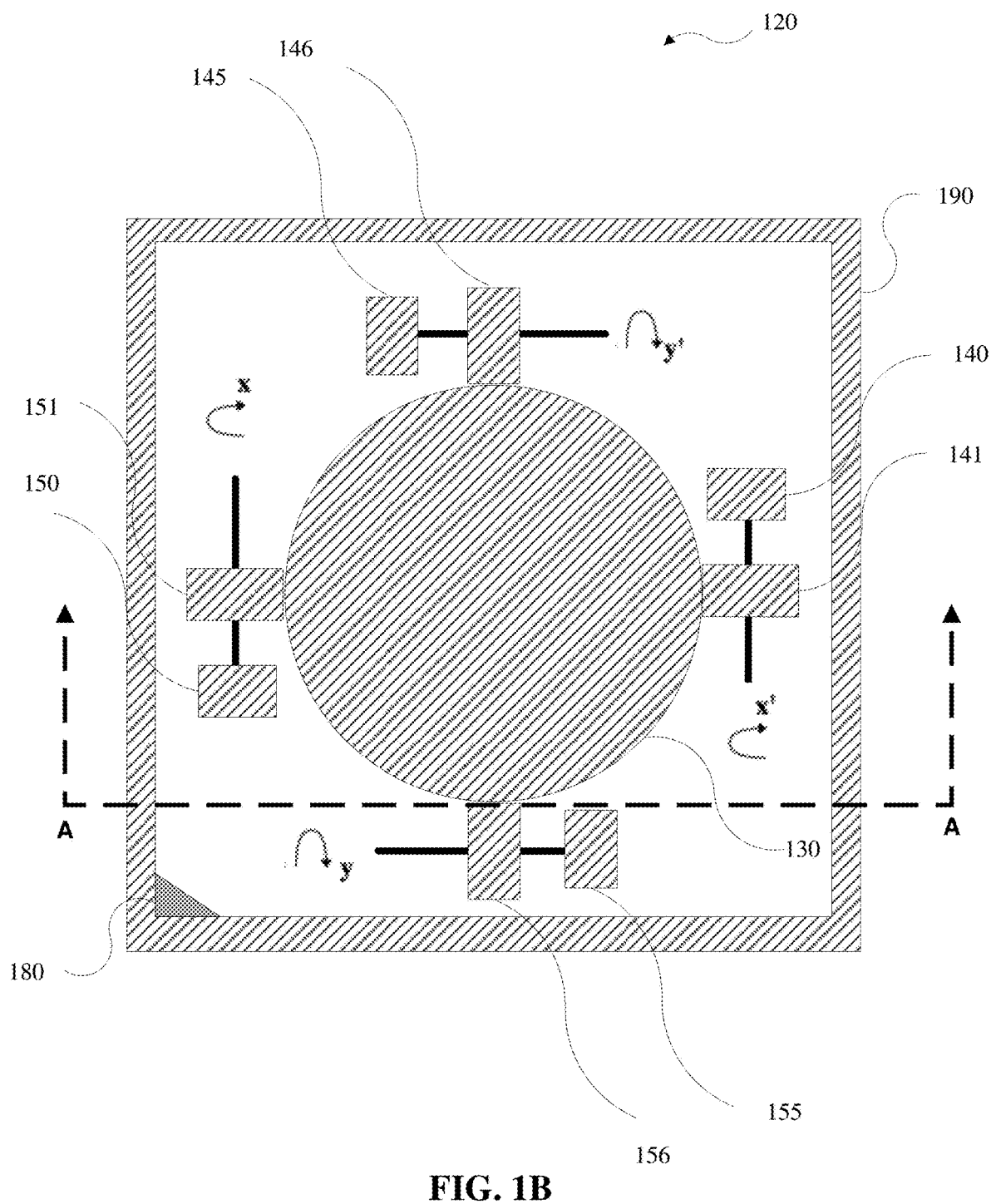
FIG. 1B illustrates an exemplary cross sectional depiction of a movement unit with a sphere, motors, and sensors.
Figure 1C:
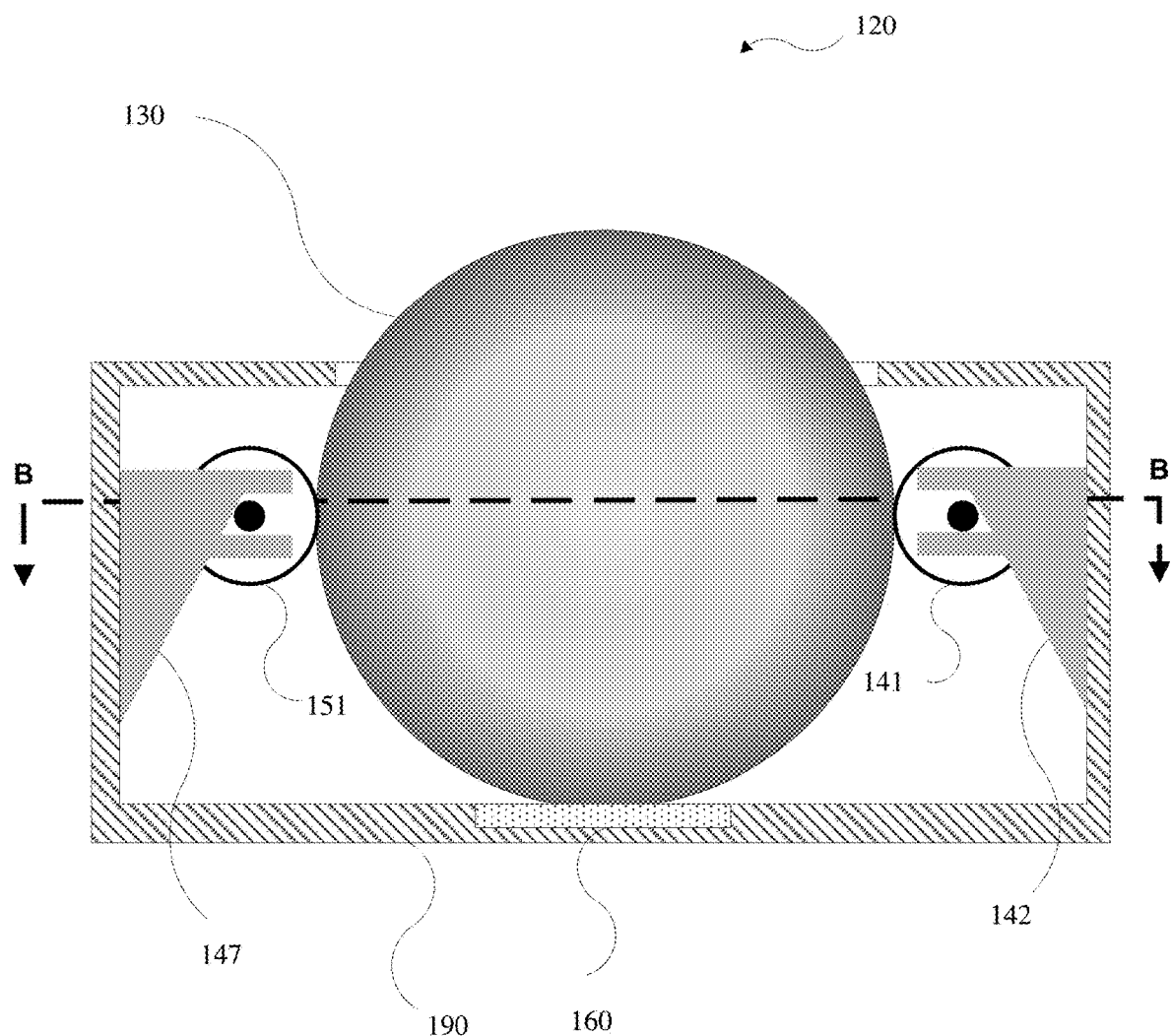
FIG. 1C illustrates an exemplary cross sectional depiction of a movement unit with a sphere, and rollers.

FIG. 1A is an exemplary depiction of a movement platform 100 with a plurality of movement units (e,g, 120, 121, and 123). FIG. 1B and FIG. 1C are exemplary cross sectional depictions of movement unit (such as movement unit 120). FIG. 1B is a cross section of movement unit 120 at cross section line B and FIG. 1C is a cross section of movement unit 120 at cross section line A. Referring to FIG. 1A, FIG. 1B, and FIG. 1C, in some embodiments, each movement unit can include a sphere 130, a first motor 140, a second motor 145, a first sensor 150, a second sensor 155, a third sensor 160, and/or one or more rollers 141, 146, 151, and 156. In some embodiments, each movement unit could include a shell 190, an orientation marker 180, and support arms 142 and 147. Examples of sphere 130 include a plastic sphere, a rubber sphere, a metal ball bearing, a metal sphere coated in rubber, etc.

As they are illustrated in FIG. 1A, the plurality of movement units (e,g, 120, 121, and 123) are configured in a grid pattern in movement platform 100. For example, the grid could be aligned as a square pattern, a staggered pattern, or a hexagonal pattern. FIG. 1A shows an exemplary square pattern. In some embodiments, the grid includes of a plurality of movement units (e,g, 120, 121, and 123). In some embodiments, shell 190 encloses one or more other components of movement unit 120. In some embodiments, shell 190 abuts, but does not necessarily contact, sphere 130 to form a top surface of movement unit 120 with the exposed portion of sphere 130 with sphere 130 extending above shell 190. For example, when viewed from above (as illustrated here, opposite sensor 160 with regard to sphere 130), a top surface of shell 190 could look like a square plate with a hole cut out of it. From the top of movement unit 120 only a portion of sphere 130 would be visible. In some embodiments, shell 190 does not directly come into contact with sphere 130; a small gap may be maintained between the inner edge of a hole on the top of shell 190 and sphere 130. In some embodiments, the top surface of movement platform 100 may be comprised of a plethora of adjoined movement units. Movement units 120 are shown as a square shape, but could also be other shapes, such as a hexagonal movement unit.

In some embodiments, orientation marker 180 is used to ensure the proper orientation of each movement unit. For example, if all movement units are oriented in the same way, then each orientation marker 180 may be in the bottom left corner of each movement unit 120. In some embodiments, orientation markers 180 are used to ensure that horizontal force and speed readings of sensors 150 and 155 are reading in the proper direction. This could facilitate easy replacement of broken or defective movement units 120 in movement platform 100.

As illustrated, movement unit 120 includes a sphere capable of being rotated by motors 140 and 145. An exposed portion of sphere 130 may act as a contact surface for a user interacting with movement unit 120. In some embodiments, a number of rollers, for example rollers 141, 146, 151, and 156, may abut sphere 130. Four rollers are shown and discussed, but other numbers of rollers may be used. In some embodiments, rollers 141, 146, 151, and 156 are used to keep sphere 130 in place while it is rotating. In some embodiments, one or more support arms, such as support arm 142 and 147, may be used to keep rollers 141, 146, 151, and 156 in place. Other support mechanisms and configurations are possible.

In some embodiments, motors are attached to two or more of rollers 141, 146, 151, and 156. For example, motor 140 and motor 145 could be attached to rollers 141 and 146 respectively. The motor 140 and motor 145 could rotate rollers 141 and 146 which in turn would rotate sphere 130.

In some embodiments, sensors are attached to one or more of rollers 141, 146, 151, and 156. For example, first sensor 150 and second sensor 155 is attached to rollers 151, and 156 respectively. The first sensor 150 and second sensor 155 could detect movement or force of rollers 151 and 156 which is translated from sphere 130.

In some embodiments, one or more movement units 120 can have one or more motors, such as first motor 140 and second motor 145, configured to rotate sphere 130 (e.g., by rotating rollers 141 and 146). For example, first motor 140 could be capable of rotating sphere 130 around a first axis of rotation and second motor 145 could be capable of rotating sphere 130 around a second axis of rotation, where the second axis of rotation is perpendicular to the first axis of rotation. For the purpose of this disclosure, a rotational direction around the first axis of rotation will be referred to as the X-direction, and a rotational direction around the second axis of rotation will be referred to as the Y-direction. In some embodiments, motors 140 and 145 may work in conjunction to move the spheres in other directions than strictly the X-direction or strictly the Y-direction. For example, both motors running at roughly equivalent power could rotate the sphere in a direction 45° from either the X-direction or the Y-direction.

In some embodiments, each sphere may have both a first and a second motor. In some embodiments, the motors may be distributed to the movement units such that not every movement unit has a first motor and/or a second motor. For example, some movement units may be equipped with a first motor, other units can be equipped with a second motor, and other units may not have a motor.

In some embodiments, one or more movement units 120 can have one or more rotational sensors, such as first sensor 150 and second sensor 155, configured to detect rotational force or rotation of sphere 130. Rotational force is torque, moment, or moment of force. For example, first sensor 150 could be capable of detecting rotational force or rotation of sphere 130 in a first direction and second sensor 155 could be capable of detecting rotational force or rotation of sphere 130 for a second direction, where the second direction is perpendicular to the first direction. In some embodiments, the rotational force of the sphere could be converted into a horizontal force exerted by a user, or the horizontal force exerted by the user could be translated into a rotational force of the sphere. In some embodiments, the rotational force of the sphere may be used as the horizontal force exerted by the user. In some embodiments, the reading of the forces exerted by the user or the conversion of those forces will depend on what measurements the system needs to determine a user force. For example, if a virtual reality system has a database of user movement related to horizontal forces applied by the user, then rotational forces of the spheres could be converted into horizontal forces of the user. In another example, if a database of user movement is related to rotational forces of spheres in movement platform 100, then rotational force of the spheres could be used. In some embodiments, the rotational force of sphere 130 means force imparted to sphere 130 from a user that could be recorded as rotational force. In some embodiments, the sensors may work in conjunction with motors 140 and 145. In some embodiments, the sensors can detect rotational movement and/or force of a sphere for a time period and a computer system can use this information to determine the force that would be required to cause the rotational movement and/or force of the sphere. The computer system can also record the force exerted on the sphere by motors 140 and 145 in the same time period by monitoring the energy (e.g., electricity) put into each motor. For example, each motor may have a conversion equation determining how much force output each motor produces for each unit of energy put into the motor. In some embodiments, the force exerted by motors 140 and 145 can be compared to the force recorded by the sensors to extrapolate the force the user is exerting on the sphere or determine that the user is not exerting any force on the sphere. In some embodiments, the sensors may be integrated into the motors directly. In some embodiments, the sensors may be speed sensors that detect the rotational speed of sphere 130.

In some embodiments, one or more movement units 120 can have one or more pressure (also referred to as z-directional sensors), such as third sensor 160, configured to detect force (i.e., pressure) exerted on the sensor by and/or through sphere 130. For example, a foot could step on sphere 130, where the sphere 130 in turn applies that force to third sensor 160. In some embodiments, each movement unit, such as movement units 120, 121, and 123, may include third sensor 160. In some embodiments, only some movement unit, such as movement units 120, 121, and 123 may include third sensor 160. In some embodiments, sphere 130 will rotate against third sensor 160. In some embodiments, a surface of third sensor 160 which contacts sphere 130 will include a low friction material. In some embodiments, the low friction material could be a surface coating or a pad on top of third sensor 160. In some embodiments, a low friction material is a material, such as polytetrafluoroethylene (PTFE), with a coefficient of friction that is less than 0.5.

Figure 2:
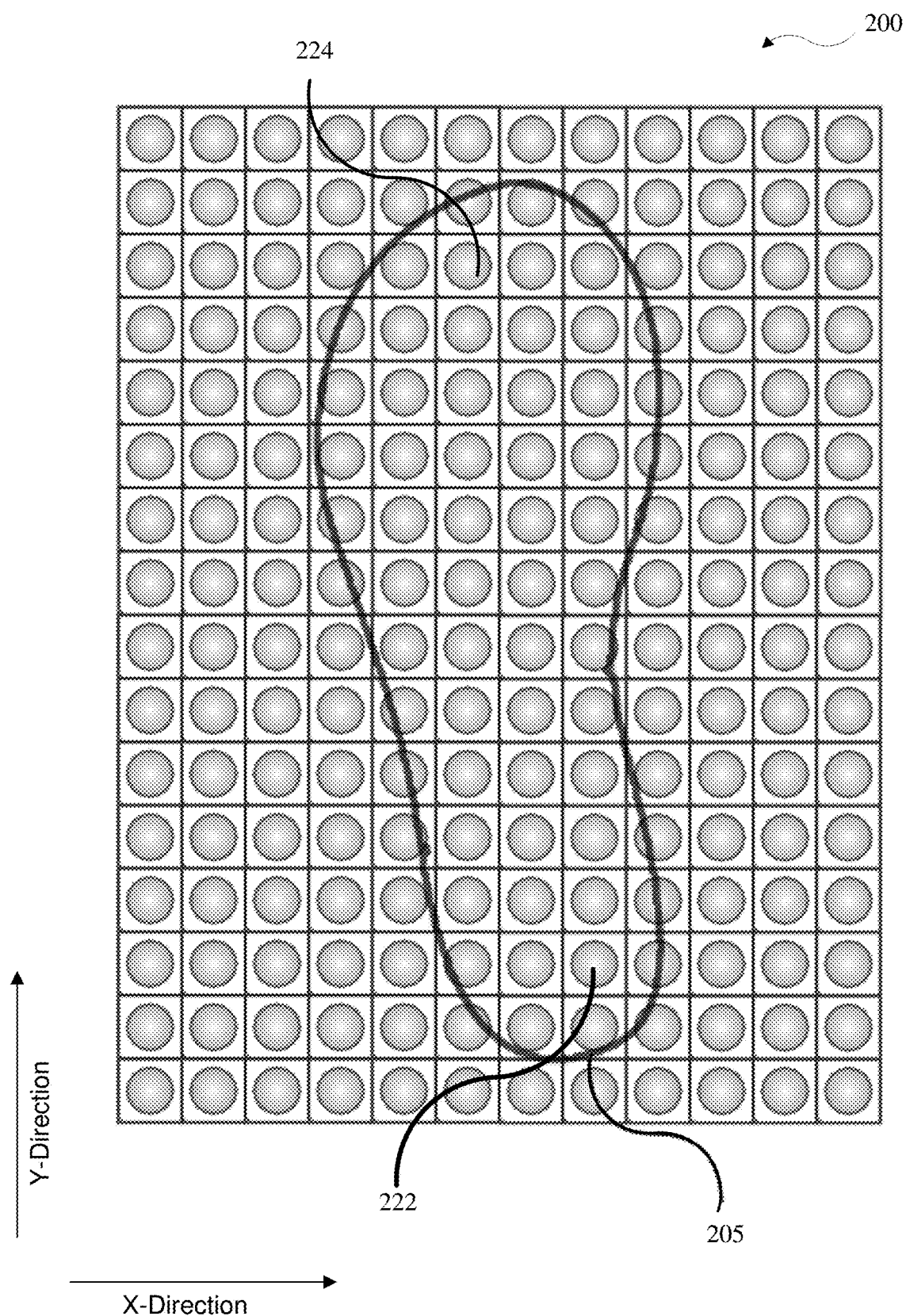
FIG. 2 illustrates an exemplary depiction of a movement platform with a plurality of movement units and an outline of a user foot.

In some embodiments, a movement platform is configured to record and transmit force data recorded by sensors. A computer system receiving the data can use the data received from the sensors to determine a user's position and movement. Referring to FIG. 2, outline 205 on movement platform 200 shows an approximate placement of a user's foot on platform 200. The pressure or force exerted in a Z-direction (perpendicular to the surface of movement platform 200 or, in other words, into the page) of the user's foot can be recorded by sensors (e.g., third sensor 160). Force information can be used not only to determine the force being applied by the foot, but also the approximate size of the object (in this case, a foot) applying the force. For example, if each movement unit, such as movement units 222 and 224, on platform 200 has a top surface area of 1 centimeter and 30 movement units inside of outline 205 are recording Z-force data, then the surface area, in contact with movement platform 200, of the object applying the data would be approximately 30 square centimeters. Other sensors, such as first sensor 150 and a second sensor 155, could detect horizontal (i.e., X-direction and Y-direction) movements of an object on movement platform 200. In some embodiments, it is possible for some units to detect movement or force in a positive X-direction or Y-direction at the same time as other units detect force in a negative X-direction or Y direction. For example, if a foot is rotating or twisting, the movement unit 222 near the heel could detect a positive movement or force in the X-direction while the movement unit 224 at the toes could detect a negative movement or force in the X-direction.

In some embodiments, a VR system with a movement platform that is configured to record force data could be used to create force models by combining movement information (e.g., what movement the user is performing) and force data for a user. In some embodiments, the force models could be used by a virtual reality system to aid in prediction of user movements by comparing force readings from a movement platform to force models.

Figure 3:
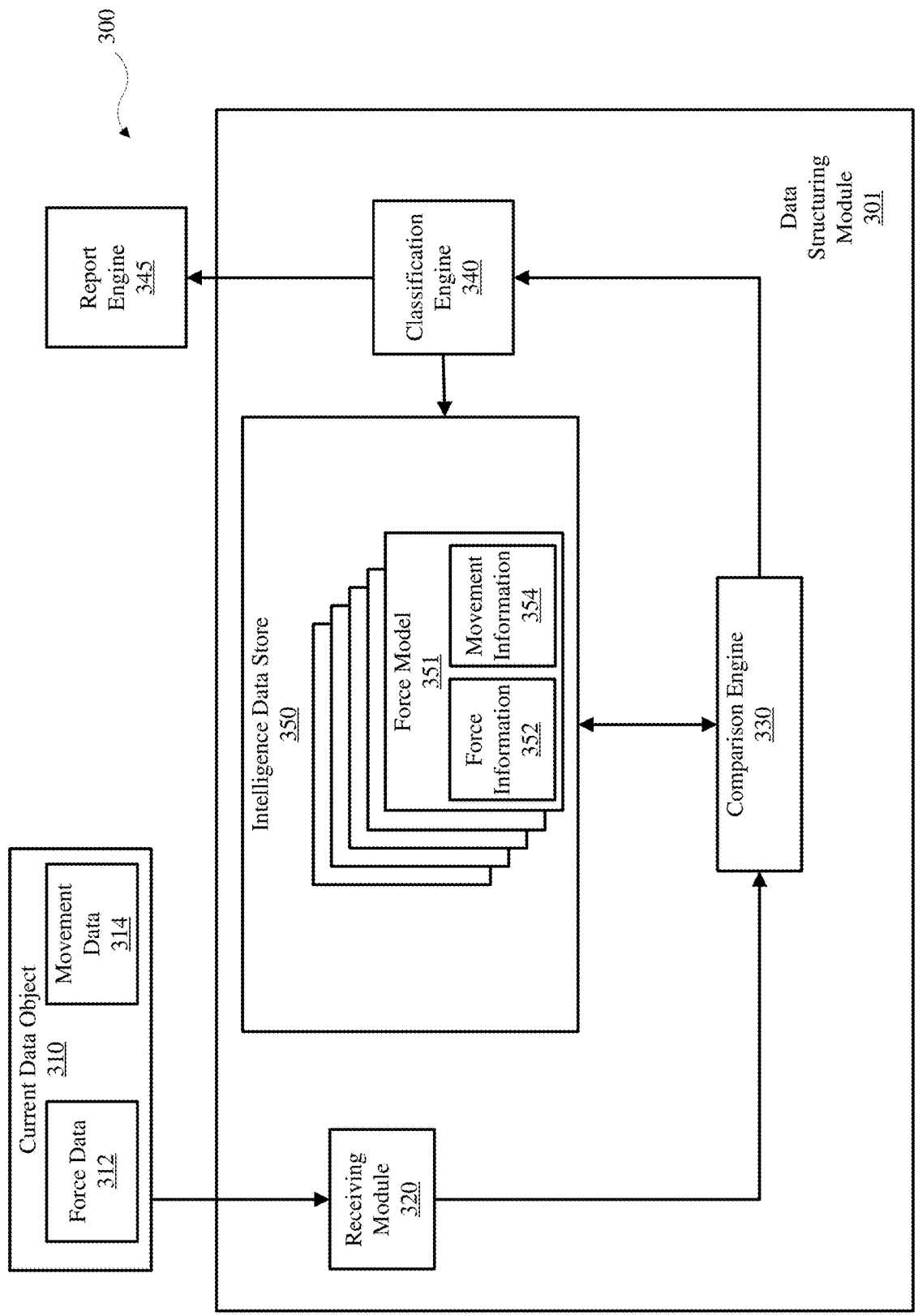
FIG. 3 is a block diagram illustrating components of a virtual reality system with an attached movement platform, according to some embodiments of the disclosure.

FIG. 3 is an exemplary block diagram of an example high level architecture of a system 300 for receiving and processing information from a movement platform. In some embodiments, a data structuring module 301 is used to create an intelligence data store 350 for a plurality of force models. In some embodiments, current data object 310 contains force data 312 and movement data 314. In some embodiments, movement data 314 contains movement information such as a video recording, 3-D image of a user, a plot of foot placement and movement, etc. Movement data could be any data that contains information of a user related to the physical presence and movement of a user during a user movement. Force data 312 is force information received from a movement platform, such as movement platform 100. For example, force data could include Z-force data, X-force data, and Y-force data. Receiving module 320 is configured to receive the data contained in current data object 310. In some embodiments, receiving module 324 is configured to parse the data to separate force data 312 and movement data 314 for one or more time periods.

In some embodiments, comparison engine 330 is configured to recognize, parse, and output structured data relating to movement data 314, such as positions of a user or positions of objects (e.g., feet) on the movement platform. In some embodiments, comparison engine 330 interprets movement data 314 and extrapolates relative positions of parts of a user. For example, a coordinate for a body part could be determined using speed and acceleration information for the body part.

In some embodiments, comparison engine 330 is configured to analyze the information received by receiving module 320 to identify forces that can be linked to certain user movements. For example, a particular set of X-forces, Y-forces, and Z-forces could be linked to a jumping movement by a user. In some embodiments, linked is the association of user exerted forces with user performed movements based on previous observations the user exerted forces and user performed movements coinciding during the same period of time. In some embodiments, after identifying possible links, comparison engine 330 can store the linked force information 352 and movement information 354 to force model 351 in intelligence data store 350. Intelligence data store 350 can contain a plurality of force models (such as force model 351). In some embodiments, comparison engine 330 can compare new force models to older force models. In some embodiments, a particular force model is compared to a plurality of other force models to determine an accuracy of the first force model.

In some embodiments, the comparison of force models can be used to improve accuracy and disregard anomalous force models. For example, if a force model does not accurately match to other force models that are based on a similar user movement, the force model may be disregarded as an anomalous result. In some embodiments, comparison engine 330 can link force models that are likely to be sequential. For example, if one force model is associated with a left foot step, a right foot step could be likely to follow.

In some embodiments, classification engine 340 can classify various force models. For example, the force models could be ranked according to frequency of occurrence, order of occurrence, accuracy, etc. In some embodiments, classification engine 340 could also determine a probability that the force models in intelligence data store 350 could be used to accurately depict user movement by comparing force data from a user to the force models in intelligence data store 350. For example, classification engine 340 might determine that there is too wide of a variance between the force models related to jumping. In such an example, the accuracy of jumping depictions may be increased if more movement data 314 and related force data 312 related to a user jumping were available to classification engine 340.

In some embodiments, reporting engine 345 reports the contents of intelligence data store 350. For example, reporting engine 345 could provide one or more force models, such as force model 351, to a computer system (e.g., a VR system). In some embodiments, reporting engine 345 could also report on an estimated probability that the force models in intelligence data store 350 would be sufficient to accurately depict user movement based on only force data for that user. For example, if classification engine 340 determines that more data regarding jumping is needed, reporting engine 345 could report to a computer system that user jumping data is needed.

Figure 4:
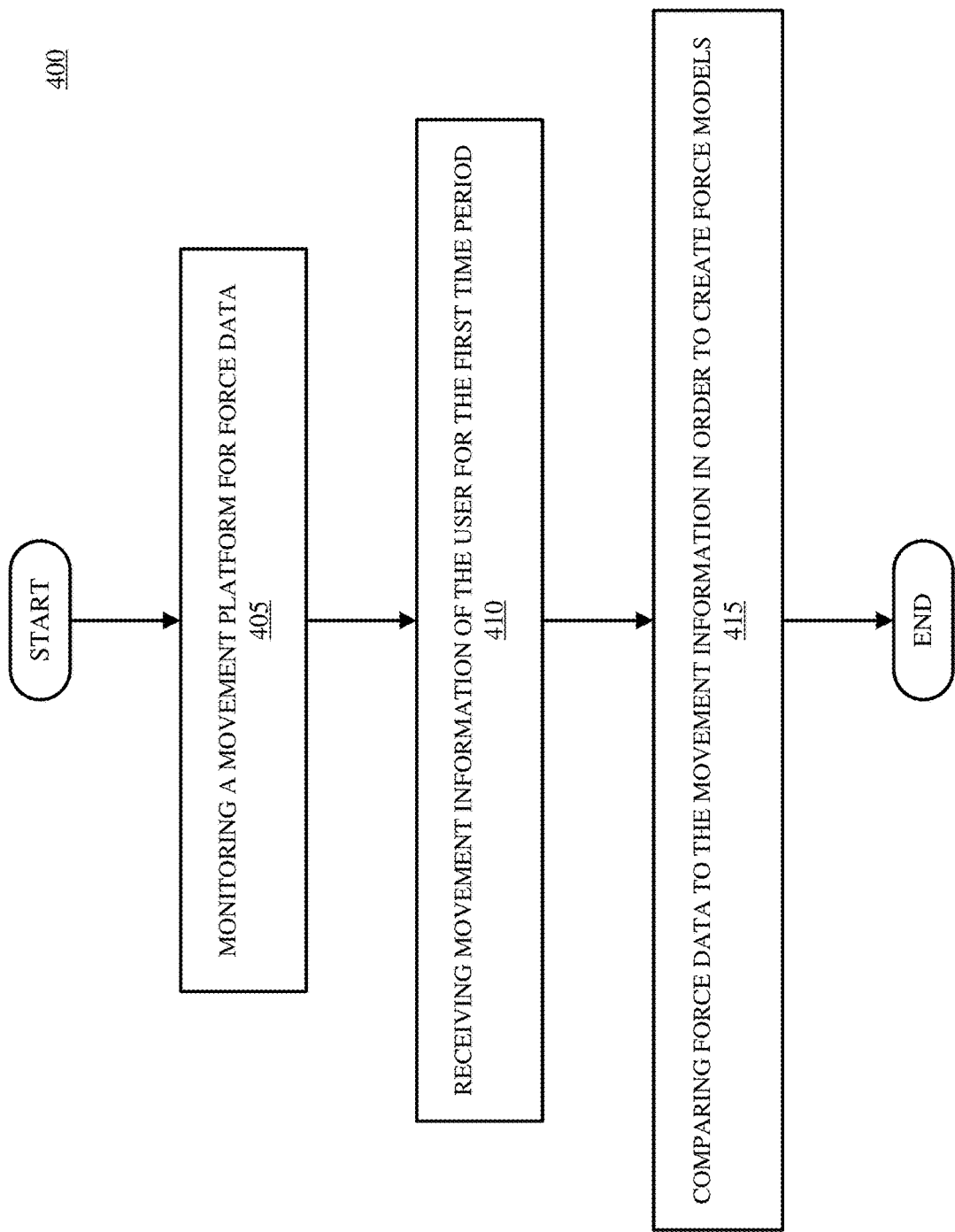
FIG. 4 is a flow diagram illustrating creation of force models according to some embodiments of the disclosure.

FIG. 4 illustrates an example method 400 by which a movement platform can be used to create force models.

In block 405 a processor monitors a movement platform for force data from a user for a first time period. A movement platform, such as movement platform 100, may record force readings while a user performs specific actions. In some embodiments, the movement platform comprises a grid of a plurality of movement units, where one of the plurality of movement units contains an X-force sensor, one of the plurality of movement units contains a Y-force sensor, and one of the plurality of movement units contains a Z-force sensor. In some embodiments, the force data includes X-force data, Y-force data, and Z-force data. The monitored or received information can then be used to train a computer system to recognize force patterns that are associated with specific unit movements.

In block 410 the processor receives movement information of the user for the first time period. For example, the movement information contains movement information such as of a video recording of a user performing an action, 3-D image of a user performing an action, a plot of foot placement and movement, etc. For example, while a user is performing an action, such as a running jump, on a moving platform, a video imaging system could be recording the user action while a movement platform is recording the force exerted by the user. Other methods for recording the user action are possible. In some embodiments, the movement information provides predicted displacement information of a user action. In some embodiments, a predicted displacement is a movement of a user if the user were unimpeded and not repositioned by a movement platform.

In block 415 force data may be compared to the movement information in order to create force models. For example, a computer system logically connected to the sensors of a movement platform could associate a specific pattern of force data to a user action such as running, jumping, walking, standing, crouching, etc. In some embodiments, the computer system could also cross link different actions to determine a combination of actions. For example, a combination of the running and jumping force patters could be linked to the action of jumping while running. Likewise, the combination of running and crouching patterns could be linked to the action of sliding.

In some embodiments, each action may be broken down into specific elements of the actions and the starting time, stopping time, and duration of each element may be recorded to compare to contemporaneously recorded force data from the movement platform. In some embodiments, the user action can be segmented into time periods and each element can be associated with a specific set of time periods, including a set of one time period, for easier comparison to the force data. For example, a user action of jumping could be divided into several separate elements. In some embodiments, the user action and associated force data could be segmented into specific time segments. For example, the elements of a jump could be a pre-jump squat taking 250 milliseconds, vertical acceleration taking 250 milliseconds, liftoff from the platform taking 250 milliseconds, and touchdown on the platform taking 250 milliseconds. In some embodiments, data structuring module 301 could segment each of these elements into 50 millisecond time periods. Following the example, each element of the jump would then have 5 time periods and the jump as a whole would have 20 time periods. In some examples, comparison engine 330 could create a force model, such as force model 351, for each time period. In some examples, some force models could include one time period while others include multiple time periods. In some embodiments, classification engine 340 could create sequential links between one force model and another. For example, if a force model was created for the pre-jump squat, that model could be linked to a force model for the vertical acceleration.

In some embodiments, force data recorded by a VR system with a movement platform may be compared to force models to determine movement information.

Figure 5:
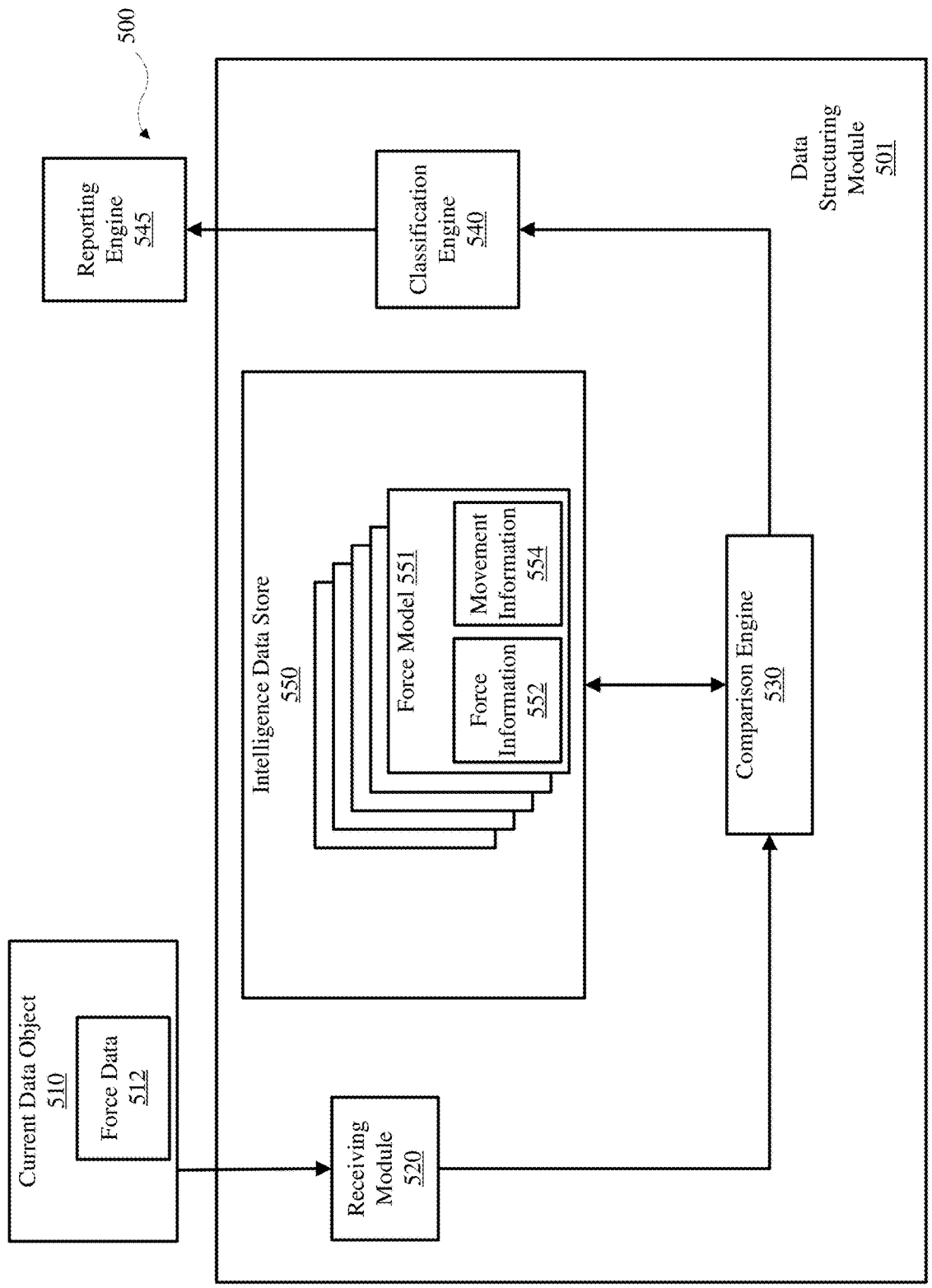
FIG. 5 is a block diagram illustrating components a virtual reality system with an attached movement platform, according to some embodiments of the disclosure.

In some embodiments, referring to FIG. 5, shown is a block diagram of an example high level architecture of a system 500 for receiving and processing information from a movement platform. In some embodiments, a data structuring module 501 is used to find a force model, such as force model 551 in intelligence data store 550, that matches force data 512. In some embodiments, current data object 510 contains force data 512. Force data 512 is force information received from a movement platform, such as movement platform 100. For example, force data could include Z-force data, X-force data, and/or Y-force data. Receiving module 520 is configured to receive the data contained in current data object 510. In some embodiments, receiving module 520 is configured to parse force data 512 for one or more time periods.

In some embodiments, comparison engine 530 is configured to recognize similarities between force data 512 and force information 552 contained in a force model such as force model 551. In some embodiments, comparison engine 530 may determine if there is a match. In some embodiments, if there is no match, reporting engine 545 may report the lack of a match to a computer system, such as a VR system.

In some embodiments, comparison engine 530 is configured to analyze the information received by receiving module 520 to identify one or more force models, such as force model 551, that match force data 512. In some embodiments, after identifying possible matches, comparison engine 530 can compile the possible matches and send them to classification engine 540.

In some embodiments, data structuring module 501 may receive a string of data objects 510 containing force data 512. As each new data object is received comparison engine 530 and classification engine 540 can work in conjunction to determine the force model or force models reported by reporting engine 545. For example, initially the force data 512 received by receiving module 520 could cause comparison engine 530 to select a running force model, a walking force model, and a sprinting force model with the classification engine 540 identifying running as the most likely. After more information is received by receiving module 520, the comparison engine 530 might be able to eliminate one or more of the models, such as the walking force model. Likewise, classification engine 540 might change its ranking by identifying the sprinting force model as the most likely.

In some embodiments, reporting engine 545 reports a selected force model, such as force model 551, with movement information 554. For example, reporting engine 545 could provide one or more force models, such as force model 551 to a computer system (e.g., a VR system). In some embodiments, reporting engine 545 could also report on an estimated probability that the force model or force models provided from intelligence data store 550 matches the force data 512 received in current data object 510.

Figure 6:
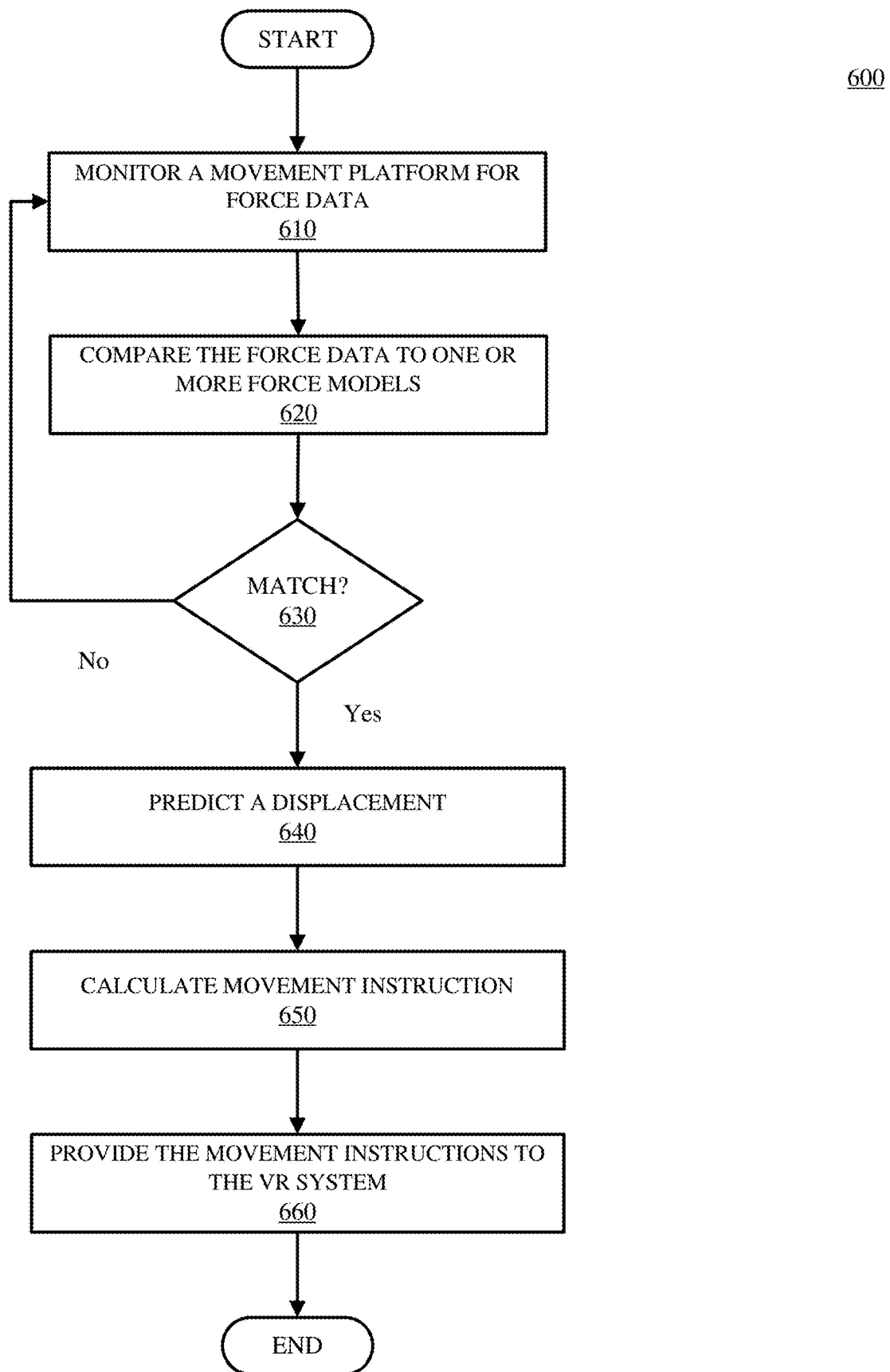
FIG. 6 is a flow diagram illustrating the matching of force models to recorded forces according to some embodiments of the disclosure.

FIG. 6 illustrates an example method 600 by which a force model can be selected based on force information received from a movement platform.

In block 610 a processor monitors a movement platform for force data from a user. In some embodiments, the movement platform may include sensors to detect force in three directions. In some embodiments, when no force is detected the process may end.

In block 620 the processor compares the force data to one or more force models in a model database connected to the processor. In some embodiments, the processor may compare the force data to all force models contained in intelligence data store 550. In some embodiments, a select group of force models may be selected for comparison based on previous comparisons. In some embodiments, the force models may be organized in a data tree structure. For example, a second force model (e.g., a second running step) and a third force model (e.g., a running jump) could be selected as the most likely force models to follow the first force model (e.g., a first running step). A fourth force model and a fifth force model could be selected as the most likely force models to follow the second force model, and a sixth force model and a seventh force model could be selected as the most likely force models to follow the third force model. In this example the first level of the data tree is the first force model, the second level of the data tree is the second force model and the third force model, and the third level of the tree includes the fourth, fifth, sixth and seventh force models.

In block 630 the processor determines that the force data matches a first force model from the one or more force models. In some embodiments, one or more force models may be a match for the force data. In some embodiments, classification engine 540 may rank the force model based on the degree of match between the force data and each force model. If a match is not found the processor will resume block 610.

In block 640 the processor predicts, based on the comparing and the determining, a predicted displacement for a user. In some embodiments, a given force pattern may include movement information 554 which may be used in conjunction with force data 512 to predict a movement or displacement of a user. For example, force model 551 could include a one-newton X-force reading for a left foot of a user and a linked one inch movement for a right foot of a user. If receiving module 520 receives force data including a two-newton X-force reading, the computer might calculate that the right foot would move two inches.

In block 650, the processor calculates, based on the predicting, movement instructions for the movement platform. In some embodiments, comparison engine 530 may calculate movement instructions for a movement platform attached to a VR system. For example, if the processor predicts that the right foot is moving two inches while not directly on the movement platform, instructions could be calculated to move the left foot back two inches.

In some embodiments, in block 660, reporting engine 545 will provide the movement instructions to the VR system. For example, once the movement instructions are calculated, the movement platform 100 could be instructed to move the left foot back two inches. Movement platform 100 could then engage the motors in the movement units (such as movement units 120, 121, and 123) under the left foot to rotate the spheres until the foot has moved two inches in the desired direction.

In some embodiments, reporting engine 545 could send 3D displacement instructions to a computing device for virtual imaging in the VR system. In some embodiments, the processor extrapolates, based on the comparing, a virtual 3D displacement for a user. In some embodiments, the processor determines, based on the extrapolating, 3D displacement instructions (i.e., how to move the user) for the movement of the user. In some embodiments, the processor may send out the 3D displacement instructions to the VR system.

Computer System

Figure 7:
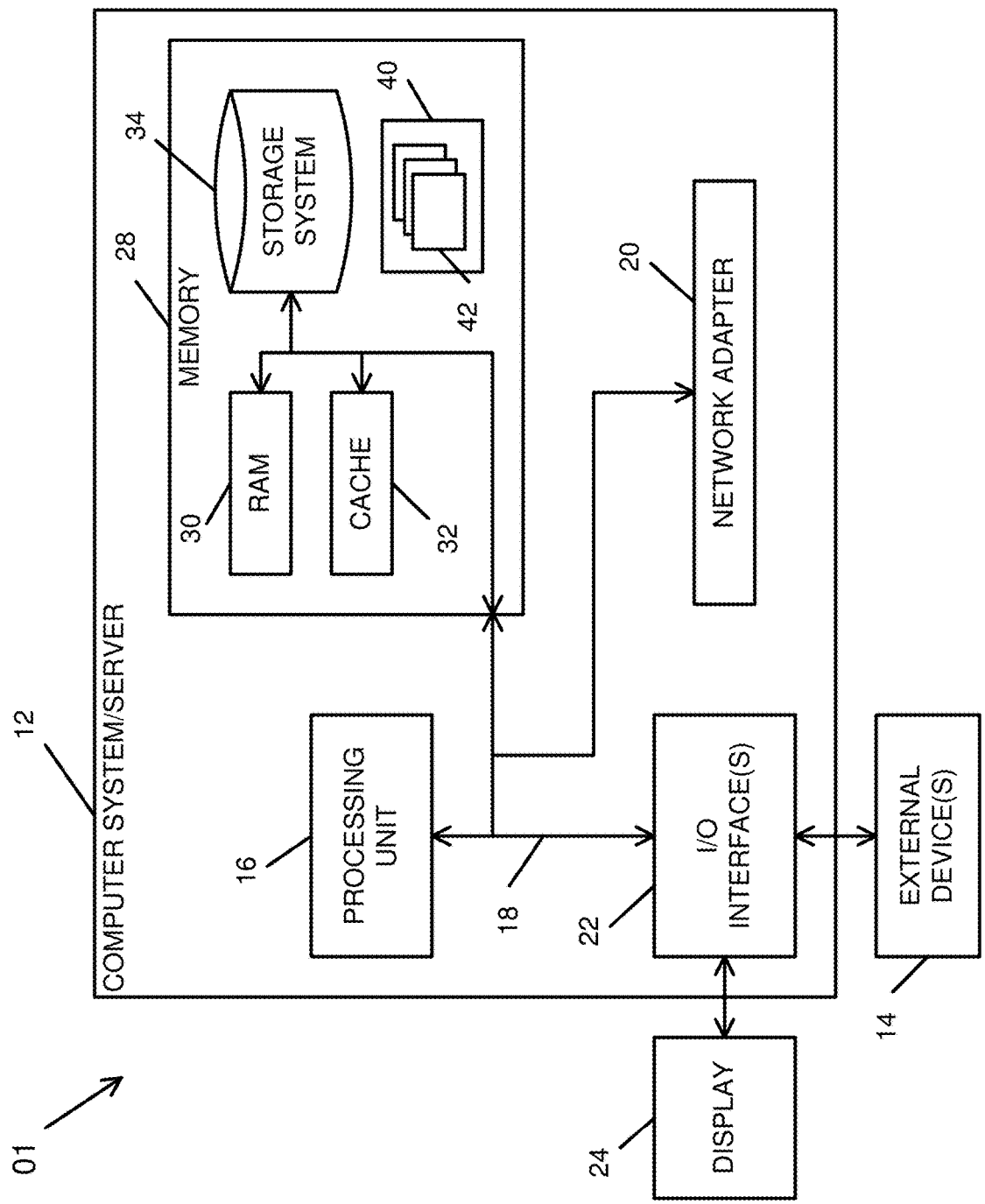
FIG. 7 depicts a computer system in accordance with an exemplary embodiment of the present invention.

In an exemplary embodiment, the computer system is a computer system 01 as shown in FIG. 7. Computer system 01 is only one example of a computer system and is not intended to suggest any limitation as to the scope of use or functionality of embodiments of the present invention. Regardless, computer system 01 is capable of being implemented to perform and/or performing any of the functionality/operations of the present invention.

Computer system 01 includes a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices.

Computer system/server 12 may be described in the general context of computer system-executable instructions, such as program modules, being executed by a computer system. Generally, program modules may include routines, programs, objects, components, logic, and/or data structures that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in computer system 01 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions/operations of embodiments of the invention.

Program/utility 40, having a set (at least one) of program modules 42, may be stored in memory 28 by way of example, and not limitation. Exemplary program modules 42 may include an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the present invention.

Computer system/server 12 may also communicate with one or more external devices 14 such as a keyboard, a pointing device, a display 24, one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems.

Cloud Computing

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
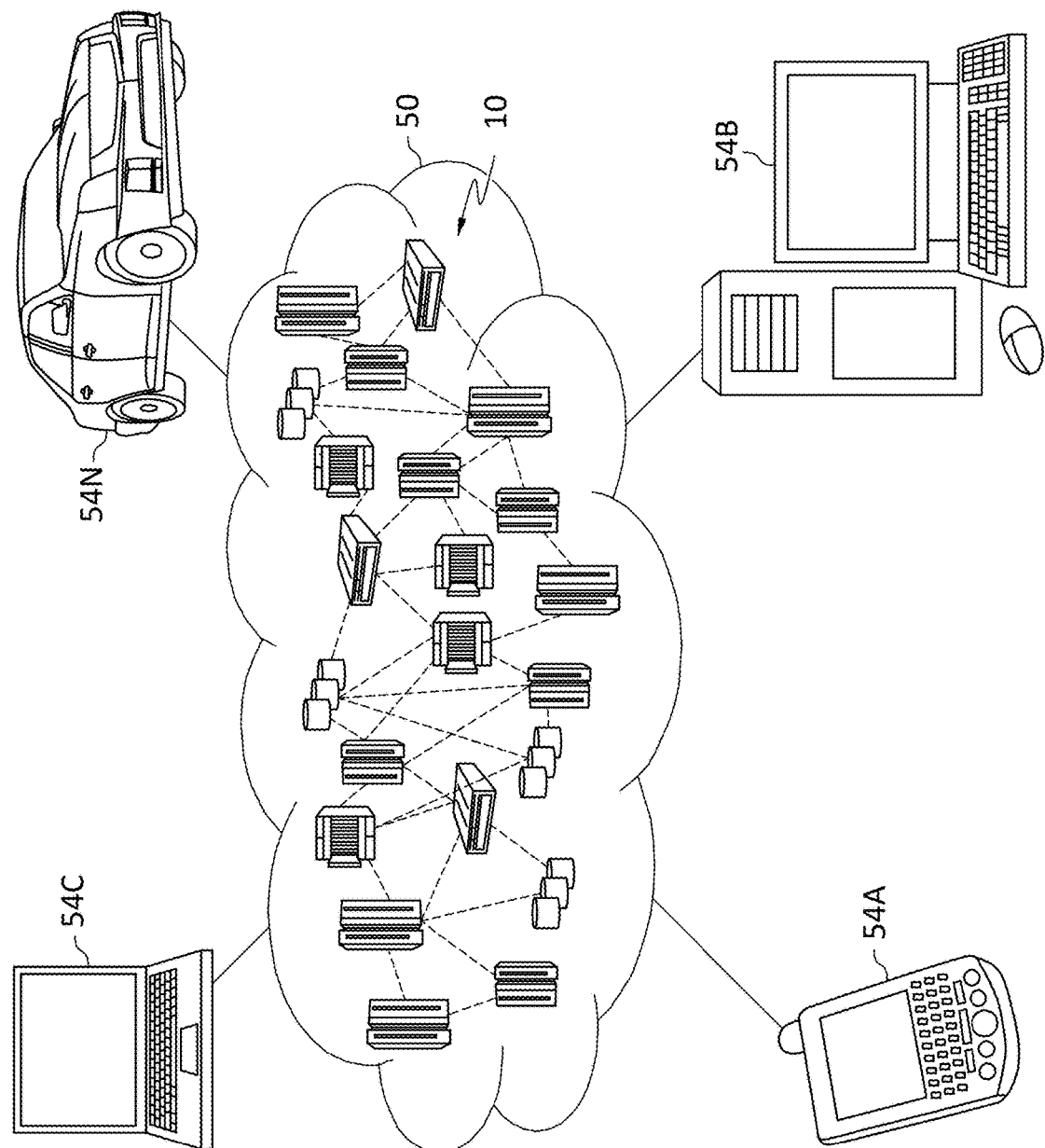
FIG. 8 depicts a cloud computing environment according to various embodiments of the present invention.

Referring now to FIG. 8, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Figure 9:
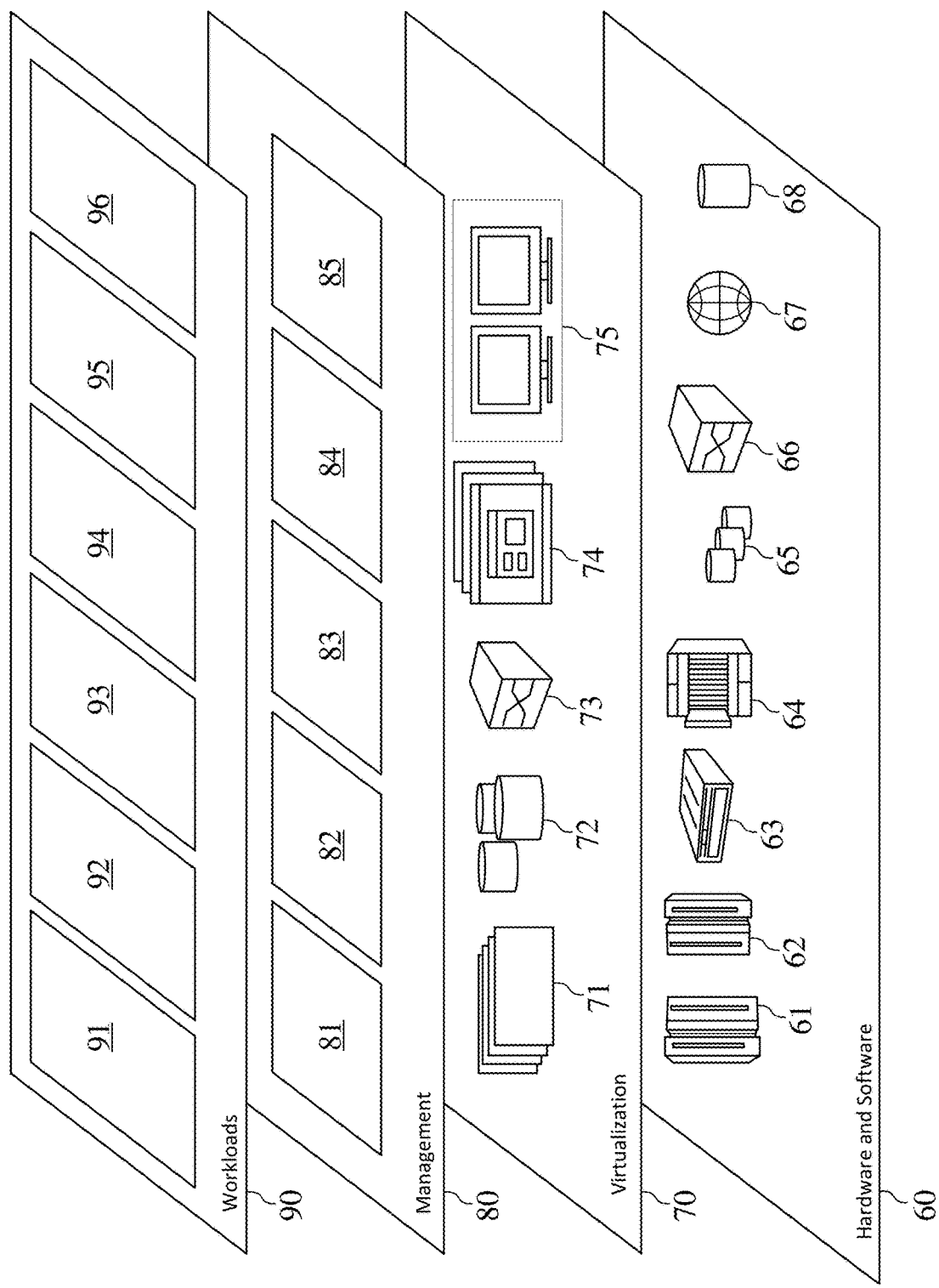
FIG. 9 depicts abstraction model layers according to various embodiments of the present invention.

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and predictive neural networks 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, a "set" of an object does not equate to all available instances of that object. For example, if four files were available, a set of files may not contain all four files. Further, as used herein, the phrase "each of a set" of an object refers only to the instances of that object of that set. For example, if four files were available, the phrase "a set of two files from the four files, each of the files in the set being read only" would properly be interpreted as implying that two files (the two files in the set) are read only. The two files of the four available files that are not in the set may or may not be read only.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed:
1. A method comprising:
monitoring, by a processor and during a first time period, a grid of a plurality of movement units on a movement platform;
detecting, by a first force sensor on a first movement unit of the plurality of movement units, force data, wherein the force data comprises a first force exerted upon the first movement unit by a first user;

receiving, by the processor, a first set of movement information of the first user for the first time period;

compiling, by the processor, the force data and the movement information into a first force model, wherein the movement information includes a first movement of the first user, and wherein the force model comprises a force pattern and associated user movement information;

comparing a second set of force data from the movement platform to the force pattern in the first force model, wherein the force pattern comprises multiple forces exerted on the plurality of movement units;

determining, based on the comparing, that the second set of force data is a match for the first force model;

estimating, based on the determining, that the user has initiated the first movement;

extrapolating, based on the estimating, movement instructions for the movement platform, wherein the movement instructions instruct the movement platform to compensate for the associated movement information, providing the movement instruction to the movement platform.

2. The method of claim 1 wherein the first force model is linked to a second force model.

3. The method of claim 1 wherein the first force model is at a first level in a data tree consisting of a plurality of force models.

4. The method of claim 1 further comprising:
sending the first force model to a computer system connected to a virtual reality system; and
predicting, by the computer system, movement of the user based on the force model.

5. The method of claim 1 wherein the force data includes rotational force information.

6. The method of claim 1 wherein the force data includes pressure information.

7. The method of claim 1 wherein the first force model is compared to a plurality of other force models to determine an accuracy of the first force model.

8. The method of claim 1, further comprising:
detecting, by the processor, a second force exerted upon a second force sensor in a second movement unit of the plurality of movement units;
comparing, by the processor, the second force and the force data;
identifying, based on the comparing, a match between the second force and the force data; and
predicting, based on the identifying, a second set of movement information for the second user.

9. A method comprising:
receiving, by a processor from a movement platform, force data of a user,
comparing, by the processor, a first pattern in the force data to one or more force models in a model database, wherein each force model includes a force pattern and associated user movement information, and
wherein the force pattern comprises multiple forces exerted on the movement platform;
determining that the first pattern in the force data matches a second pattern in a first force model from the one or more force models;
predicting, based on a user movement from the first force model, a displacement for the user;
extrapolating, based on the predicting, movement instructions for the movement platform, wherein the movement instructions instruct the movement platform to compensate for the associated movement information,
providing the movement instruction to the movement platform; and
sending, by the processor, the associated user movement information to a virtual reality system for virtual imaging.

10. The method of claim 9 further comprising:
extrapolating, by the processor and based on the comparing, a virtual 3D displacement of the user;
determining, based on the extrapolating, 3D displacement instructions, and
sending 3D displacement instructions to a computing device.

11. The method of claim 10 wherein the computing device is a virtual reality device.

12. The method of claim 9 wherein the force data includes rotational force information.

13. The method of claim 9 wherein the force data includes pressure information.

14. The method of claim 9 wherein the first force model is linked to a second force model.

15. The method of claim 9 wherein the first force model is at a first level in a data tree consisting of a plurality of force models.

16. A computer program product, the computer program product comprising a computer readable storage medium having program instructions embodied therewith, the program instructions executable by a computer to cause the computer to:
monitor, by a processor and during a first time period, a grid of a plurality of movement units on a movement platform;
detect, by a first force sensor on a first movement unit of the plurality of movement units, force data, wherein the force data comprises a first force exerted upon the first movement unit by a first user;
receive, by the processor, a first set of movement information of the first user for the first time period; and
compile, by the processor, the force data and the movement information into a first force model, wherein the movement information includes a first movement of the first user, and
wherein the force model comprises a force pattern, and associated user movement information;
comparing a second set of force data from the movement platform to the force pattern in the first force model,
wherein the force pattern comprises multiple forces exerted on the plurality of movement units;
determine, based on the comparing, that the second set of force data is a match for the first force model; and
estimate, based on the determining, that the user has initiated the first movement; and
extrapolating, based on the estimating, movement instructions for the movement platform, wherein the movement instructions instruct the movement platform to compensate for the associated movement information,
providing the movement instruction to the movement platform.

17. The computer program product of claim 16 wherein the first force model is linked to a second force model.

18. The computer program product of claim 16 wherein the first force model is at a first level in a data tree consisting of a plurality of force models.

19. The computer program product of claim 16 further comprising sending the first force model to a computer system connected to a virtual reality system.

20. The computer program product of claim 16 wherein the force data includes rotational force information.

* * * * *

UNITED STATES PATENT AND TRADEMARK OFFICE
CERTIFICATE OF CORRECTION

PATENT NO. : 10,955,907 B2
APPLICATION NO. : 16/184486
DATED : March 23, 2021
INVENTOR(S) : Chong et al.

It is certified that error appears in the above-identified patent and that said Letters Patent is hereby corrected as shown below:

On the Title Page

Item (72), Line 1, change "Jin Xa Xu" to --Jin Xu--

Signed and Sealed this
Fifteenth Day of November, 2022

Katherine Kelly Vidal
*Director of the United States Patent and Trademark Office*